US009078906B2

(12) United States Patent  
Bayer

(10) Patent No.: US 9,078,906 B2  
(45) Date of Patent: Jul. 14, 2015

(54) LOBSTER HEMOLYMPH AS A UTILITY FOR TREATMENT OF MAMMALIAN TISSUE LESIONS

(71) Applicant: Robert C. Bayer, Orono, ME (US)

(72) Inventor: Robert C. Bayer, Orono, ME (US)

(73) Assignee: Robert C. Bayer, Orno, ME (US)

( * ) Notice: Subject to any disclaimer, the term of this patent is extended or adjusted under 35 U.S.C. 154(b) by 0 days.

(21) Appl. No.: 13/815,286

(22) Filed: Feb. 16, 2013

(65) Prior Publication Data

US 2014/0234378 A1    Aug. 21, 2014  
US 2014/0348877 A9    Nov. 27, 2014

Related U.S. Application Data

(60) Provisional application No. 61/634,174, filed on Feb. 24, 2012.

(51) Int. Cl.

| | |
|---|---|
| *A61K 35/60* | (2006.01) |
| *A61K 35/64* | (2015.01) |
| *A61K 35/612* | (2015.01) |
| *A61Q 19/00* | (2006.01) |
| *A61K 9/00* | (2006.01) |
| *A61K 35/63* | (2015.01) |
| *A61K 8/98* | (2006.01) |

(52) U.S. Cl.  
CPC ............. *A61K 35/64* (2013.01); *A61K 8/987* (2013.01); *A61K 9/00* (2013.01); *A61K 35/612* (2013.01); *A61K 35/63* (2013.01); *A61Q 19/00* (2013.01)

(58) Field of Classification Search  
None  
See application file for complete search history.

(56) References Cited

U.S. PATENT DOCUMENTS 5,231,081 A * 7/1993 Stiefel et al. ............... 514/19.3  
2011/0033499 A1    2/2011 Cuthbertson

OTHER PUBLICATIONS

Casares, Federico M. et al; "The american lobster, *Homarus americanus* contains morphine that is coupled to nitric oxide release in its nervous and immune tissues: evidence for neurotransmitter and hormonal signaling." Neuroendocrin. Let. (2005) 2(26) p. 89-97.*  
Beale, K. M. et al; "Anit-lipopolysaccharide factors in the american lobster *Homarus americanus*: Molecular characterization and transcriptional response to vibro fluvialis challenge." Comp. Biochem. Physiol. Part D (2008) 3 p. 263-269.*  
Bollag, W. and Ott, F.; "Retinoic acid: topical treatment of senile or actinic keratoses and basal cell carcinomas." Agents and Actions (1970) 1/4 p. 172-175.*  
Press release from the FDA, Nov. 28, 1995, http://archive.hhs.gov/news/press/1995pres/951128a.html.*  
Cancer drug information, www.cancer.gov/cancertopics/druginfo/fda-imiquimod, downloaded Feb. 20, 2014.*  
http://dtp.nci.nih.gov/timeline/noflash/milestones/m4_nixon.htm, downloaded Feb. 20, 2014.*  
Jemal, Ahmedin et al; "Cancer statistics, 2010." CA Cancer J. Clin. (2010) 60 p. 277-300.*  
dictionary.com entry for lobster, downloaded Feb. 19, 2014.*  
Degrave, Sammy et al; "A classification of living and fossil genera of decapod crustaceans." Raffles Bulletin of Zoology (2009) Supl. No. 21, 1-109.*  
Schoenback, Emanuel B. et al; "Observations on the effects of the folic acid antagonists, aminopterin and amethopterin, in patients with advanced neoplasms." Cancer (1952) 5 p. 1201-1220.*  
Jeffes III, Edward W. B. and Tang, Emily H.; "Actinic keratosis, current treatment options." Am. J. Clin. Dermatol. (2000) 1(3) p. 167-179.*  
Proksch, Ehrhardt et al; "The skin: an indispensable barrier." Exp. Dermatol. (2008) 17 p. 1063-1072.*  
Dolashka et al., "Antitumor Activity of Glycosylated Molluscan Hemocyanins via Guerin Ascites Tumor," 2011, pp. 130-149, Immunological Investigations.  
Linn et al., "Keyhole Limpet Haemocyanin in Experimental Bladder Cancer," 2000 , Abstract Only, ProQuest, Aquatic Sciences and Fisheries Abstracts.  
The Lobster Conservancy, "Lobster Biology: Physiological Processes," retrieved from http://www.lobsters.org/tlcbio/biology5.html, 1 page. Date unknown, Downloaded 2004.  
Olicard et al., "Putative antiviral activity in hemolymph from adult Pacific oysters, *Crassostrea gigas*," 2005, pp. 147-152, Science Direct, Antiviral Research, vol. 66.  
Olicard et al., In vitro research of anti-HSV-1 activity in different extracts from Pacific oysters *Crassostrea gigas*, 2005, pp. 141-147, Diseases of Aquatic Organisms, vol. 67.  
Pan et al., "A review on digestive enzymes in crustacean," 2002, Abstract Only, Journal of Ocean University of Qingdao/Qingdao Haiyang Daxue Xuebao.  
Pan et al., "A review on digestive enzyme of crustacean larvae," 2006, Abstract Only, Journal of fishery sciences of China/Zhongguo Shuichan Kexue.  
Liu et al., "Antiviral immunity in crustaceans," 2009, pp. 79-88, Fish & Shellfish Immunology, vol. 27.  
Lee et al., "Early events in crustacean innate immunity," 2002, pp. 421-437, Fish & Shellfish Immunology, vol. 12.  
Zhang et al., "Antiviral properties of hemocyanin isolated from shrimp *Penaeus monodon*," 2004, pp. 93-99, Science Direct, Antiviral Research vol. 61.  
Greco et al., "Antiviral activity of the hemolymph of *Lonomia obliqua* (Lepidoptera: Saturniidae)," 2009, Abstract Only, PubMed, Antiviral Research, vol. 84.  
Velkova et al., "Structure of hemocyanin from garden snail *Helix lucorum*," 2010, Abstract Only, PubMed, Comparative Biochemistry Physiology.  
Zanjani et al., "Formulation of abalone hemocyanin with high antiviral activity and stability," 2014, Abstract Only, European Journal of Pharmaceutical Sciences, vol. 53.

* cited by examiner

*Primary Examiner* — Maury Audet  
*Assistant Examiner* — Fred Reynolds  
(74) *Attorney, Agent, or Firm* — Hoffman Warnick LLC

(57) ABSTRACT

The invention is crustacean hemolymph as a utility for the pharmaceutical and/or cosmetic treatment of viral and other neoplastic or pre-neoplastic mammalian tissue lesions. The method comprises topically administering to mammalian tissue a formula that is made from lobster hemolymph—neat; or lobster hemolymph extracts; or lobster hemolymph in combination with certain carriers, binders; or as an adjuvant. The hemolymph may be from various species of lobster, *Homarus americanus* in particular.

14 Claims, No Drawings

LOBSTER HEMOLYMPH AS A UTILITY FOR TREATMENT OF MAMMALIAN TISSUE LESIONS

CROSS-REFERENCE TO RELATED APPLICATIONS

This application claims the benefit of U.S. Provisional Patent Application No. 61/634,174, filed 24 Feb. 2012.

BACKGROUND OF THE INVENTION

Technical Field

The invention relates to use of crustacean hemolymph (particularly but not exclusively from lobster), or active extracts thereof or compounds therewith, to impact mammalian immune systems through topical treatments of viral and neoplastic skin lesions and wound healing.

In the *Homarus americanus* circulatory system the heart is a single-chambered sac consisting of striated muscles with several openings called ostia. It is suspended in and surrounded by a blood sinus called the pericardium which lies directly above the pyloric stomach on the dorsal (upper) surface of the animal, just under the carapace. Invertebrates have a dorsally positioned circulatory system and a ventral nerve cord, whereas vertebrates have a ventrally located circulatory system and a dorsal nervous system. The blood, or hemolymph, passes from the pericardium, through the ostia, and into the heart. At the beginning of a contraction, the ostia close (via ostial flaps), the intracardial pressure increases, which opens the cardioarterial valves so that the heart can empty. Blood is pushed into the major arteries, most of which are directed forward to supply sensory organs and vital systems. Arteries also run toward the abdomen, both ventrally and dorsally, to supply blood to the pereiopods, ventral nerves, gut, and abdominal muscles. From these arteries the blood enters sinuses, or blood cavities. These sinuses bathe the various organs. No veins are present to return the blood to the heart. Instead, blood returns to the heart via interconnecting spaces known as venous sinuses which open back into the pericardium. Because of this architecture, the lobster's circulatory system is known as an "open" system. After contraction, the heart muscle relaxes, intracardiac pressure drops, the cardioarterial valves close, the heart is distended by action of the ligaments, the ostia open, and the hemolymph enters from the pericardium. (Lobster Conservancy, 2004)

Hemolymph in arthropods is composed of water, inorganic salts (mostly $Na^+$, $Cl^-$, $K^+$, $Mg^{2+}$, and $Ca^{2+}$), and organic compounds (mostly carbohydrates, proteins, and lipids). Hemocytes are free-floating cells within the hemolymph. They play a role in the arthropod immune system, which resides in the hemolymph.

Lobster hemolymph contains metalloproteins (proteins that include a metallic ion), most notably the oxygen-carrying hemocyanin (similar to human hemoglobin, but containing copper rather than iron). Hemocyanins are chromoprotein and account for more than 90% of all the crustacean hemolymph protein. Hemocyanins occur as hexamers composed of six heterogeneous monomeric subunits. Each subunit holds an active site of two coppers, with only one corresponding oxygen molecule. Recent studies show hemocyanins provide important immune functions in crustaceans. (Pan, 2008)

Hemolymph from mollusk and arthropods has been show to have antiviral properties. It is not known how the hemolymph interacts with tissue to produce this effect. However, it is known that the immune system of arthropods resides in the hemolymph and the hemocytes within the hemolymph play a role, which may be part of the explanation. Immune systems protect organisms from foreign substances, also known as non-self materials, including pathogens.

Unlike vertebrates, invertebrates such as crustaceans do not have immune memory or adaptive immunity; rather they rely on innate or natural immune responses. Innate immune systems are "phylogenetically a more ancient defense mechanism and can be found in all multicellular organisms. This system is the first line of defense that helps to limit infection at an early stage, and relies on germ line encoded receptors that recognizes conserved molecular patterns present on microorganisms." (Young, 2002) According to Soderhall, one such innate reaction in crustaceans is "the clotting process, which is very efficient and rapid and consists of a clotting protein [belonging to the vitellogenin superfamily of proteins] present in plasma and a transglutaminase in the blood cells." (Soderhall, 1999)

Crustacean hemocytes play an important role in immune reactions, and "are capable of phagocytosis, encapsulation, nodule formation, and mediation of cytotoxicity." (Soderhall, 1992)

This is a summary of some related work:

Regarding the species Abalone—*Haliotis asinine*, a study has been conducted on effects of hemolymph and components on the following viruses: HIV, H1N1, Human papilloma virus, Herpesvirus, and rhinovirus. (Patent—USPTO—20110033499)

Regarding the species Buckmoth—*Lepidoptera: saturniidae*, a study has been conducted on effects of hemolymph on the following viruses: measles, H1N1, and polio. (Greco, 2009)

Regarding the species, Shrimp—*Penaeus monodon* a study has been conducted on effects of component hemocyanin on the following virus: White Spot Virus (Zhang, 2003)

Regarding the species, Snail—*Rapana venosa*, a study has been conducted on effects of hemolymph on the following virus: Herpesvirus. (Dolashka-Angelova, 2009)

Regarding the species Oyster—*Crassostrea gigas*, a study has been conducted on effects of hemolymph on the following viruses: Herpesvirus, Pancreatic necrosis virus. (Olicard, 2005)

Hemocyanin extracted from keyhole limpet hemolymph been shown to be effective in treating bladder cancer. (Linn et al, 2000)

Hemocyanin and arylphorin from arthropod species *Eurypelma, Limulus, Astacus, Carcinus* and *Calliphora* have been shown to be possible treatments for tumors in warm-blooded animals (Stiefel, et al. Patent—U.S. Pat. No. 5,231,081)

Broad antiviral activity was found in tissues of crustacean (Blue crab—*Callinectes sapidus*, Shrimp—*Penaeus setiferus*, and crayfish—*Procambarus clarkia*) affecting Sindbis virus, vaccinia virus, vesicular stomatitis virus, mengo virus, banzie virus and poliomyelitis (Pan, 2000)

All publications mentioned in this specification are herein incorporated by reference. Any discussion of documents, acts, materials, devices, articles, or the like that has been included in this specification is solely for the purpose of providing a context for the present invention. It is not to be taken as an admission that any or all of these matters form part of the prior art base or were common general knowledge in the field relevant to the present invention as it existed anywhere before the priority date of this application.

SUMMARY OF INVENTION

The inventions provides a formulation and process for utilizing hemolymph from the lobster (particularly but not exclusively *Homarus americanus*), and extracts thereof and compounds therewith, as topical treatment and/or an ameliorant for both viral and neoplastic or pre-neoplastic tissue lesions, and wound healing The invention relates to preparations, including but not limited to: liquids; ointments; slurries, powders; and/or crystals made using crustacean hemolymph with a variety of ancillary compounds, including but not limited to carageenans, starches, gelatins, vitamins, aloe, proteins, glycerins, parabens, crustacean shell powder, mineral oils, and plant oils. The hemolymph is rendered in particular but not exclusively from the lobster genus:species *Homarus americanus*.

DETAILED DESCRIPTION OF THE INVENTION

Hemolymph from the lobster, particularly but not exclusively *Homarus americanus* is utilized (neat or with active fragments extracted or in compounds) for the treatment in mammals of viral (such as *Molluscum contagiosum, Verruca vulgaris*—commonly known as warts, among others) and tissue neoplastic or pre-neoplastic lesions (such as ephelides, solar lentigos—commonly known as sun spots, and actinic keratosis, among others). By "neat" it is meant the hemolymph is in the form collected from the lobster, and by "active fragments" it is meant a fragment or fragments of the hemolymph that stimulate an immune response.

Typically, the mammal treated will be human. The treatment can also be applied to other mammals such as those in the bovine, porcine, ovine, equine, canine, or feline families, among others. Preparation may involve partial drying of whole hemolymph or plasma to produce a slurry.

The hemolymph can be incorporated into a cosmetic or pharmaceutical compound together with a suitable carrier or carriers i.e. carageenans, starches, gelatins, vitamins, aloe, proteins, glycerins, parabens, crustacean shell powder, mineral oils, and plant oils.

In non-clinical testing, various skin lesions were exposed to lobster hemolymph neat or absorbed into fibrous absorptive material attached to adhesive tape. It was found that the topical hemolymph treatment had an atrophic and/or fading effect on said lesions. It is not known how the hemolymph interacts with tissue to produce his effect. However, it is known that the immune system of arthropods resides in the hemolymph and the hemocytes within the hemolymph play a role, which may be part of the explanation.

The following examples provide further descriptive details of the invention:

Example 1

Extraction of Hemolymph from American Lobster (*Homarus americanus*)

Hemolymph is extracted using a variety of methods, including but not limited to:
1.1. needle and syringe to pierce the pericardial membrane to draw directly from circulatory system;
1.2. using a knife or scalpel to lance the soft tissue allowing blood flow to a catch basin or bottle;
1.3. by separating the thorax (body) from the abdomen (tail) thus opening the circulatory system at the pericardium and draining the hemolymph into a catch basin or bottle.

Example 2

Treatment of *Molluscum Contagiosum* with *Homarus americanus* Hemolymph—Neat. Anecdotal Study A juvenile female human suffering from *molluscum contagiosum* lesions treated with neat hemolymph ("neat" is defined as that form of hemolymph extracted directly from the lobster) in a dose 0.5 ml for 5 days. The treated lesion atrophied over the course of the treatment period, whereas, adjacent lesions remained unchanged during that same time period.

Example 3

Treatment of an Actinic Lesion with *Homarus americanus* Hemolymph—Neat. Anecdotal Study An adult male human with a facial actinic lesion was treated with neat hemolymph in a dose of 0.5 ml for approximately 10 days. Before the hemolymph was administered the lesion was prepared by lightly abrading the affected epidermis. The lesion initially blanched and then and appeared to atrophy over the course of the treatment.

Example 4

Treatment of *Verruca vulgaris* with *Homarus americanus* Hemolymph—Neat. Anecdotal Study An adult male human with a manifestation of the virus *Verruca vulgaris* (a common wart) topically treated the lesion with neat hemolymph in a dose of 0.5 ml sporadically over two weeks. Over the course of treatment the wart softened and atrophied.

Example 5

Treatment of *Herpes zoster* with *Homarus americanus* Hemolymph—Neat. Anecdotal Study An adult female exhibiting a rash from the virus *Herpes zoster* (shingles) topically treated the rash with neat hemolymph in a dose of approximately 0.5 ml and noticed considerable reduction is redness, itchiness and swelling in a 12 hour period.

BRIEF DESCRIPTION OF THE DRAWINGS

NA

REFERENCES

Cuthbertson, Adrian—Inventor. 2011. Original Assignee: MARINE BIOTECHNOLOGY AUSTRALIA PTY LTD. Current U.S. Classification: 424/208.1; 424/204.1; 424/209.1; 424/229.1; 424/230.1; 424/231.1; 514/3.7; 514/3.8; 514/4.2

Dolashka P, Velkova L, Iliev I, Beck A, Dolashki A, Yossifova L, Toshkova R, Voelter W, Zacharieva S. 2003. Antitumor activity of glycosylated molluscan hemocyanins via Guerin ascites tumor. Eur Urol.; 37 Suppl 3:34-40. (Institute of Organic Chemistry, Bulgarian Academy of Sciences, G. Bonchev 9, Sofia 1113, Bulgaria. pda54@abv.bg)

Greco K N, Mendonça R M, Moraes R H, Mancini D A, Mendonça R Z. 2004. Antiviral activity of the hemolymph of Lonomia obliqua (Lepidoptera: Saturniidae). Antiviral Res. February; 61(2):93-9.

Linn J F, Black P, Derksen K, Rübben H, Thüroff J W. 2009. Keyhole limpet haemocyanin in experimental bladder cancer: literature review and own results. Antiviral Res. October; 84(1):84-90. Epub 2009 Aug. 7. (Department of Urology, Johannes Gutenberg University of Mainz, Germany. jflinn@compuserve.com)

Lobster Conservancy. 2004. Retrieved from http://www.lobsters.org/ticbio/biology5.html Olicard C, Didier Y, Marty C, Bourgougnon N, Renault T. 2005. In vitro research of anti-HSV-1 activity in different extracts from Pacific oysters *Crassostrea gigas*. Dis Aquat Organ. 2005 Nov. 9; 67(1-2):141-7. PMID: 16385820

Olicard C, Renault T, Torhy C, Benmansour A, Bourgougnon N. 2005. Putative antiviral activity in hemolymph from adult Pacific oysters, *Crassostrea gigas*. Antiviral Res. June; 66(2-3):147-52. Epub April 26.

Pan. 2008. PAN, L., & JIN, C. (2008). A review on hemocyanins of crustacean. *Journal of Fisheries of China/Shuichan Xuebao*, 32(3), 484-491. Retrieved from http://search.proquest.com.prxy4.ursus.maine.edu/docview/883018286?accountid=14583

Pan, J., Kurosky, A., Xu, B., Chopra, A. K., Coppenhaver, D. H., Singh, I. P., & Baron, S. 2000. Broad antiviral activity in tissues of crustaceans. Antiviral Research, 48(1), 39-47. Retrieved from http://search.proquest.com.prxy4.ursus.maine.edu/docview/17741569?accountid=14583

Soderhall, K. 1999. Review of crustacean immunity. Retrieved from http://search.proquest.com.prxy4.ursus.maine.edu/docview/18106793?accountid=14583

Soderhall, K., & Cerenius, L. 1992. Crustacean immunity. Annual Review of Fish Diseases, 2, 3-23. Retrieved from http://search.proquest.com.prxy4.ursus.maine.edu/docview/15681912?accountid=14583 Abstract (summary)

Stiefel, T., Porcher, H., Markl, J., —Inventors. 1993. Use of hemocyanins and arylphorins to influence the immune system and for the treatment of tumors. U.S. Pat. No. 5,231,081

Young Lee, S., & Soederhaell, K. 2002. Early events in crustacean innate immunity. Fish & Shellfish Immunology, 12(5), 421-437. doi: http://dx.doi.org/10.1006/fsim.2002.0420

Zhang X, Huang C, Qin Q. 2003. Antiviral properties of hemocyanin isolated from shrimp *Penaeus monodon*. (Key Laboratory of Marine Biogenetic Resources, The Third Institute of Oceanography, State Oceanic Administration, 361005, Xiamen, PR China.)

We claim:

1. A method of treating a viral skin lesion, comprising administering to mammalian epidermis a topical formula that comprises lobster hemolymph, wherein the lobster hemolymph is extracted from one or more of *Homarus americanus, Homarus gammarus*, and *Panulirus argus*.

2. A method as claimed in claim 1, wherein the hemolymph is neat.

3. A method as claimed in claim 1, wherein the hemolymph is 95% to 100% pure.

4. A method as claimed in claim 1, wherein the hemolymph is an active ingredient combined with binders or carriers.

5. A method as claimed in claim 1, wherein the hemolymph is used as an adjuvant to an existing treatment of viral skin lesions, by topical administration to mammalian epidermis.

6. A method as claimed in claim 1, wherein the hemolymph is extracted by piercing the pericardial membrane of *Homarus americanus* and drawing hemolymph into an attached syringe.

7. A method as claimed in claim 1, wherein the hemolymph is extracted by lancing the soft tissue of *Homarus americanus* to allow hemolymph to flow into a catch basin or bottle.

8. A method as claimed in claim 1, wherein the hemolymph is extracted by separating the thorax from the abdomen of *Homarus americanus* to open the circulatory system and allow hemolymph to drain into a catch basin or bottle.

9. A method as claimed in claim 1, wherein the hemolymph is extracted by piercing the pericardial membrane of *Homarus gammarus* and drawing hemolymph into an attached syringe.

10. A method as claimed in claim 1, wherein the hemolymph is extracted by lancing the soft tissue of *Homarus gammarus* to allow hemolymph to flow into a catch basin or bottle.

11. A method as claimed in claim 1, wherein the hemolymph is extracted by separating the thorax from the abdomen of *Homarus gammarus* to open the circulatory system and allow hemolymph to drain into a catch basin or bottle.

12. A method as claimed in claim 1, wherein the hemolymph is extracted by piercing the pericardial membrane of *Panulirus argus* and drawing hemolymph into an attached syringe.

13. A method as claimed in claim 1, wherein the hemolymph is extracted by lancing the soft tissue of *Panulirus argus* to allow hemolymph to flow into a catch basin or bottle.

14. A method as claimed in claim 1, wherein the hemolymph is extracted by separating the thorax from the abdomen of *Panulirus argus* to open the circulatory system and allow hemolymph to drain into a catch basin or bottle.

* * * * *